US010448915B2

(12) United States Patent
De Man et al.

(10) Patent No.: US 10,448,915 B2
(45) Date of Patent: Oct. 22, 2019

(54) SYSTEM AND METHOD FOR CHARACTERIZING ANATOMICAL FEATURES

(71) Applicant: General Electric Company, Schenectady, NY (US)

(72) Inventors: Bruno Kristiaan Bernard De Man, Clifton Park, NY (US); Jed Douglas Pack, Glenville, NY (US); Eri Haneda, Niskayuna, NY (US); Sathish Ramani, Niskayuna, NY (US); Jiang Hsieh, Brookfield, WI (US); James Vradenburg Miller, Clifton Park, NY (US); Peter Michael Edic, Albany, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/633,819

(22) Filed: Jun. 27, 2017

(65) Prior Publication Data
US 2018/0368781 A1 Dec. 27, 2018

(51) Int. Cl.
A61B 6/00 (2006.01)
A61B 6/03 (2006.01)
(Continued)

(52) U.S. Cl.
CPC ............ *A61B 6/5217* (2013.01); *A61B 5/004* (2013.01); *A61B 5/055* (2013.01); *A61B 6/469* (2013.01);
(Continued)

(58) Field of Classification Search
USPC ........................................................ 382/131
See application file for complete search history.

(56) References Cited

U.S. PATENT DOCUMENTS 5,961,457 A 10/1999 Raylman et al.
7,203,267 B2 4/2007 De et al.
(Continued)

FOREIGN PATENT DOCUMENTS

WO 2015058044 A1 4/2015

OTHER PUBLICATIONS

Surti et al., "A Multiscanner Evaluation of PET Image Quality Using Phantom Studies", IEEE Nuclear Science Symposium Conference Record, Oct. 19-25, 2003.
(Continued)

*Primary Examiner* — Justin P. Misleh

(57) ABSTRACT

A method for characterizing anatomical features includes receiving scanned data and image data corresponding to a subject. The scanned data comprises sinogram data. The method further includes identifying a first region in an image of the image data corresponding to a region of interest. The method also includes determining a second region in the scanned data. The second region corresponds to the first region. The method further includes identifying a sinogram trace corresponding to the region of interest. The sinogram trace comprises sinogram data present within the second region. The method includes determining a data feature of the subject based on the sinogram trace and a deep learning network. The method also includes determining a diagnostic condition corresponding to a medical condition of the subject based on the data feature.

18 Claims, 7 Drawing Sheets

(51) Int. Cl.
*G06T 7/00* (2017.01)
*A61B 5/055* (2006.01)
*A61B 5/00* (2006.01)

(52) U.S. Cl.
CPC .......... *A61B 6/5205* (2013.01); *G06T 7/0012* (2013.01); *A61B 6/032* (2013.01); *G06T 2207/10072* (2013.01); *G06T 2207/20081* (2013.01); *G06T 2207/20084* (2013.01)

(56) References Cited

U.S. PATENT DOCUMENTS

| | | |
|---|---|---|
| 2003/0076988 A1 | 4/2003 | Liang et al. |
| 2010/0215140 A1 | 8/2010 | Sauer et al. |
| 2012/0141006 A1 | 6/2012 | Koehler et al. |
| 2013/0296701 A1 | 11/2013 | Zalev et al. |
| 2013/0301894 A1 | 11/2013 | Bruder et al. |
| 2015/0065864 A1 | 3/2015 | Sharma |
| 2015/0117733 A1* | 4/2015 | Manjeshwar ......... G06T 11/005 382/131 |
| 2017/0061629 A1* | 3/2017 | Zhu .................. G06T 5/007 |
| 2018/0263585 A1* | 9/2018 | Weiss .................. A61B 5/4824 |

OTHER PUBLICATIONS

Chang et al., "Realistic Simulation of Reduced-Dose CT With Noise Modelling and Sinogram Synthesis Using DICOM CT Images", Medical Physics, http://scitation.aip.org/content/aapm/journal/medphys/41/1/10.1118/1.4830431, vol. 41, Issue 1, Jan. 2014.

Zhang et al., "Computed Tomography Sinogram Inpainting With Compound Prior Modelling Both Sinogram and Image Sparsity", IEEE Transactions on Nuclear Science, vol. 63, Issue 5, pp. 2567-2576, Oct. 2016.

Comaniciu, et al, "Machine Learning Based Vesselness Measurement for Coronary Artery Segmentation in Cardiac CT Volumes", Proceedings of SPIE—The International Society for Optical Engineering, Mar. 1-4, 2011.

* cited by examiner

SYSTEM AND METHOD FOR CHARACTERIZING ANATOMICAL FEATURES

BACKGROUND

Embodiments of the present specification relate generally to automatic detection and characterization of anatomical, physiological and pathological features using medical imaging modalities and more particularly to, systems and methods for detecting and characterizing anatomical, physiological and pathological features by processing scanned data by deep learning technique.

Various imaging systems (also referred to as modalities) such as CT (computed tomography), MRI (magnetic resonance imaging), X-ray systems, US (ultrasound), and PET (positron emission tomography) are used for acquiring image datasets and generating images of anatomical structures of individuals for screening and evaluating medical conditions. Each imaging modality may provide unique advantages over other modalities for screening and evaluating certain types of diseases, medical conditions, functional or anatomical abnormalities, including, for example, cardiomyopathy, colonic polyps, aneurisms, lung nodules, calcification on heart or artery tissue, cancer micro calcifications or masses in breast tissue, and various other lesions or abnormalities. Some of the imaging techniques are also useful in other applications such as non-destructive testing in industrial applications.

Manual review and evaluation of medical images is employed by medical professionals to identify region of interest in the medical image and diagnose potential medical conditions. In general, medical images may be processed to automatically identify the anatomy and automatically assess the diagnostic quality of the medical image. Automated decision support for medical imaging includes extracting feature data from the image data, and automatically performing anatomy identification, view identification and/or determining a diagnostic quality of the image data, using the extracted feature data. Similarly, CT image datasets acquired during inspection from an aircraft engine may be used for extracting feature data representative of structural defects of the engine.

Emerging machine learning techniques such as deep learning networks are increasingly being used from the image datasets to extract anatomical features that are useful in examining the anatomy under consideration and diagnosing the underlying medical conditions of the subject.

BRIEF DESCRIPTION

In accordance with one aspect of the invention, a method is disclosed. The method includes receiving scanned data and image data corresponding to a subject. The scanned data comprises sinogram data. The method further includes identifying a first region in an image of the image data corresponding to a region of interest. The method also includes determining a second region in the scanned data. The second region corresponds to the first region. The method further includes identifying a sinogram trace corresponding to the region of interest. The sinogram trace comprises sinogram data present within the second region. The method includes determining a data feature of the subject based on the sinogram trace and a deep learning network. The method also includes determining a diagnostic condition corresponding to a medical condition of the subject based on the data feature.

In accordance with one aspect of the invention, a system for characterizing anatomical features is disclosed. The system includes a data acquisition unit configured to acquire scanned data and image data corresponding to a subject, from a computed tomography detector. The scanned data includes sinogram data. The system further includes an image processor communicatively coupled to the data acquisition unit and configured to identify a first region in an image of the image data corresponding to a region of interest in the subject. The image processor is further configured to determine a second region in the scanned data. The second region corresponds to the first region. The image processor is further configured to determine a sinogram trace corresponding to the region of interest. The sinogram trace comprises sinogram data present within the second region. The system also includes a deep learning network communicatively coupled to the image processor and configured to determine a data feature of the subject based on the sinogram trace. The deep learning network is further configured to determine a diagnostic condition corresponding to a medical condition of the subject based on the data feature.

In accordance with another aspect of the invention, a computed tomography imaging system is disclosed. The computed tomography imaging system includes an x-ray source configured to emit x-ray beam towards an organ during examination of a subject. The computed tomography imaging system further includes a computed tomography detector configured to receive the emitted x-ray beam attenuated by the region to generate scanned data. The computed tomography imaging system also includes a data acquisition unit configured to acquire the scanned data from the computed tomography detector. The scanned data includes sinogram data. The computed tomography imaging system further includes an image processor communicatively coupled to the data acquisition unit and configured to generate image data by reconstructing the scanned data. The image processor is further configured to identify a first region in an image of the image data corresponding to a region of interest in the subject. The image processor is further configured to determine a second region in the scanned data. The second region corresponds to the first region. The image processor is further configured to determine a sinogram trace corresponding to the region of interest. The sinogram trace comprises sinogram data present within the second region. The computed tomography imaging system also includes a deep learning network communicatively coupled to the image processor and configured to determine a data feature of the subject based on the sinogram trace. The deep learning network is further configured to determine a diagnostic condition corresponding to a medical condition of the subject based on the data feature.

In accordance with another aspect of the invention, a non-transitory computer readable medium having instructions to enable at least one processor module is disclosed. The instruction enable the at least one processor module to receive scanned data and image data corresponding to a subject. The scanned data comprises sinogram data. The instructions further enable the at least one processor module to identify a first region in an image of the image data corresponding to a region of interest in the subject. The instructions also enable the at least one processor module to determine a second region in the scanned data. The second region corresponds to the first region. The instructions further enable the at least one processor module to determine a sinogram trace corresponding to the region of interest. The sinogram trace comprises sinogram data present within the second region. The instructions also enable the at least one processor module to determine a data feature of the subject based on the sinogram trace and a deep learning network. The instructions further enable the at least one processor module to determine a diagnostic condition corresponding to a medical condition of the subject based on the data feature.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

As will be described in detail hereinafter, systems and methods are presented for automatic detection and characterization of anatomical, physiological and pathological features of a subject using medical imaging systems. More particularly, the systems and methods are configured for detecting and characterizing anatomical, physiological and pathological features by processing scanned data using deep learning technique.

The term "scanned data" generally refers to data acquired by an imaging system during examination of the subject. Further, the examination procedure is commonly referred to as "scanning". The scanned data generated by different imaging systems, correspond to different physical mechanisms used for scanning and require a variety of interpretations. In embodiments disclosed herein, the scanned data correspond to raw data such as, but not limited to, sinogram data, k-space data, and photon count data. Specifically, the scanned data includes a plurality of two-dimensional (2D) projections (also referred to as "sinograms") corresponding to the subject. The scanned data is further processed by a variety of image reconstruction techniques to generate image data that are presented to medical professionals for screening, diagnosis and therapy evaluation. Specifically, the image data includes a plurality of cross sectional images corresponding to the subject. The term "scanned data" may also refer to other types of data corresponding to the subject and acquired by the scanner, but does not include the reconstructed image data. The terms "feature," "anatomical feature" and "data feature" are used equivalently and interchangeably to indicate at least one of an anatomical, physiological and pathological details of the subject under examination. Specifically, the data feature may refer to one of a structural detail of an anatomical organ, a functional detail corresponding to physiology of an anatomical organ or a diagnostic detail of a medical condition related to the anatomical organ. It may be noted that the term "data feature" corresponds to a parameter derived based on the scanned data.

Figure 1:
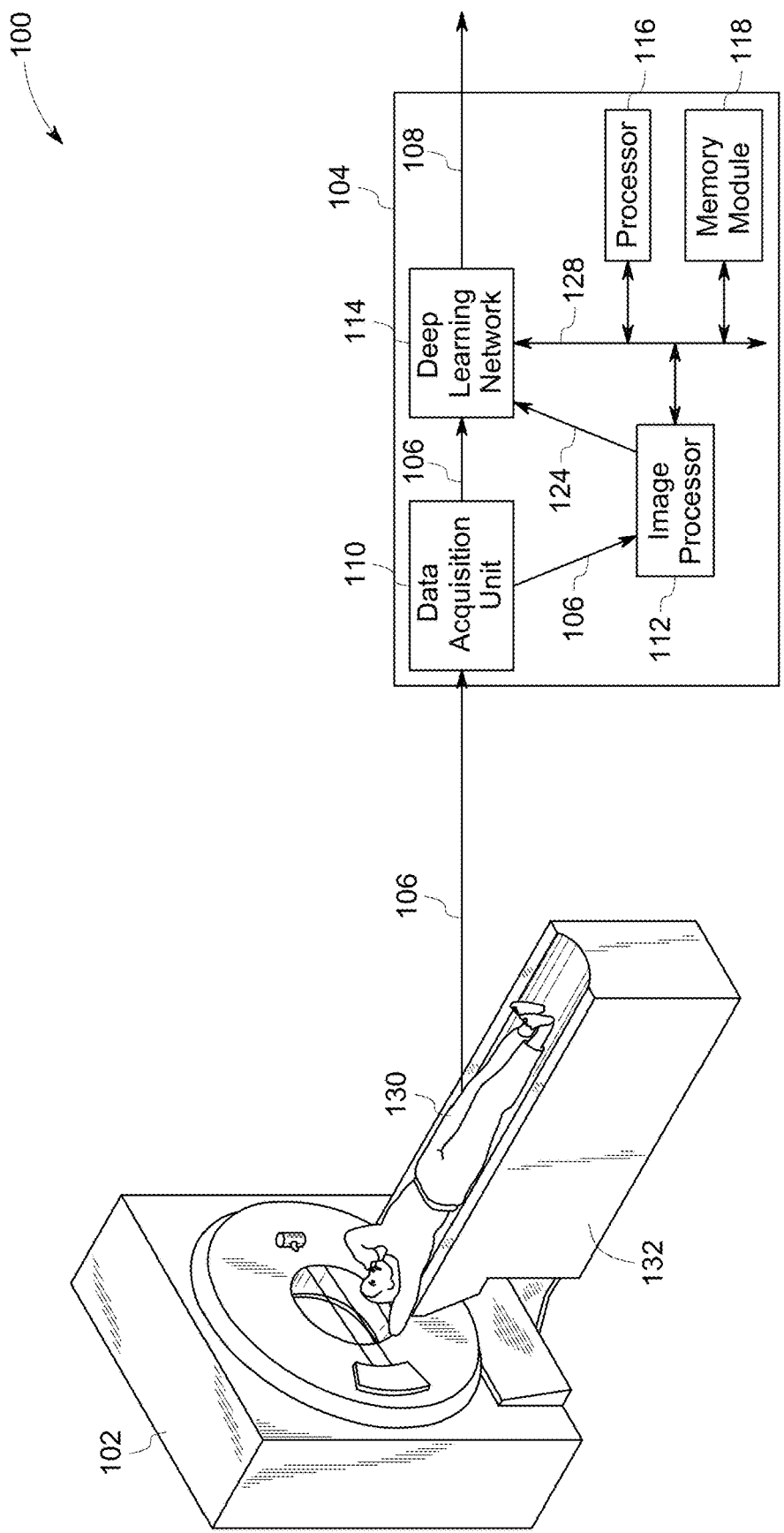
FIG. 1 is a diagrammatic illustration of a system for characterization of data features in accordance with an exemplary embodiment.
Figure 2:
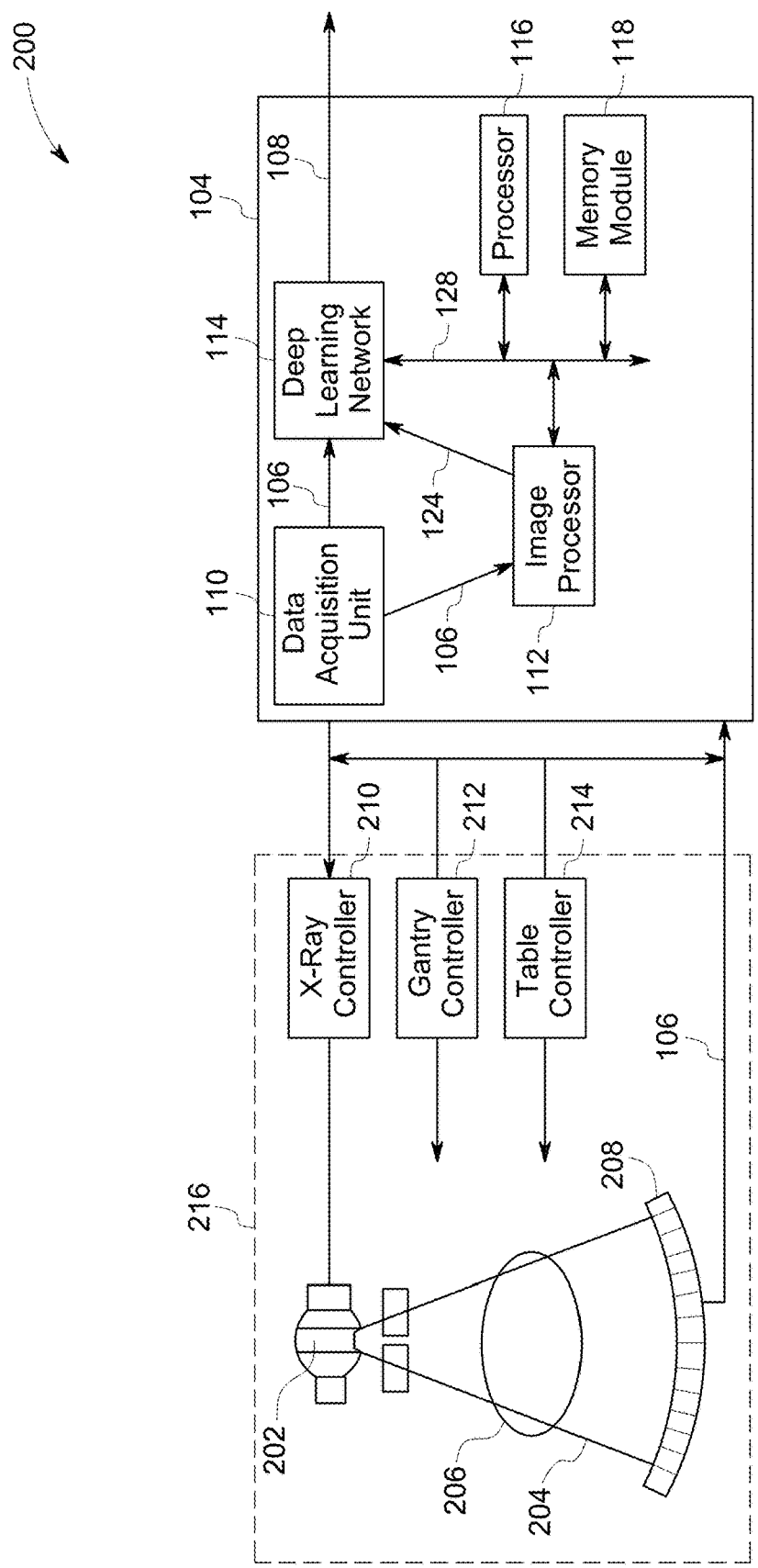
FIG. 2 is a diagrammatic illustration of a CT system for characterization of data features in accordance with an exemplary embodiment.

Turning now to FIGS. 1 and 2, FIG. 1 illustrates an imaging system 100 for characterization of anatomical features, and FIG. 2 is a schematic representation of a computed tomography (CT) imaging system 200, which is an example of the imaging system 100, in accordance with an exemplary embodiment of the present application. Both the imaging systems 100 and 200 employ a diagnostic sub-system 104. The imaging system 100 may be an ultrasound system, a CT imaging system, a magnetic resonance imaging (MM) system, a positron emission tomography (PET), NMRI (nuclear magnetic resonance imaging) system, or an X-ray system. The imaging system 100, such as a CT imaging system, includes a gantry 102 coupled to a patient table 132 configured to perform scanning of a subject 130 to generate scanned data represented by reference numeral 106. In one embodiment, the imaging system 100 may be a portable ultrasound system. In one embodiment, the scanned data is representative of photon counts acquired from a plurality of detector elements of a CT detector. In another embodiment, the scanned data is representative of sinogram data corresponding to the CT imaging system. In another embodiment, the scanned data is representative of k-space data acquired from an MRI system. In yet another embodiment, the scanned data is representative of a plurality of x-ray images from an x-ray machine. The diagnostic sub-system 104 is communicatively coupled to the gantry 102 and configured to receive the scanned data 106 from the gantry 102. The diagnostic sub-system 104 is further configured to generate a diagnostic output 108 of the scanned data 106. In one embodiment, the diagnostic output 108 is a data feature representative of at least one of a feature of an anatomical organ, a feature of a physiological condition related to the anatomical organ, and a feature of a pathological condition corresponding to the anatomical organ. Further, the diagnostic output 108 may also provide or facilitate characterization of the anatomical feature. In some embodiments, the diagnostic output 108 may include data assisting reliable diagnosis of a medical condition associated with the subject. In some other embodiments, the diagnostic sub-system 104 is configured to generate the diagnostic output 108 representative of a treatment plan corresponding to a medical condition of the subject 130.

The CT imaging system 200 includes a CT scanner 216 communicatively coupled to the diagnostic sub-system 104. The CT scanner 216 includes an x-ray source configured to emit an x-ray beam 204 towards an object such as an organ of interest during examination of a subject. In one embodiment, the x-ray beam 204 is a fan beam and in another embodiment, the x-ray beam is a cone beam. The CT scanner further includes a computed tomography detector 208 configured to receive the emitted x-ray beam attenuated by an organ 206 of the subject 130 of FIG. 1 to generate scanned data 106. The computed tomography detector 208 includes an array of detector elements configured to sense the projected x-rays that pass through the organ 206. In one embodiment, a physical object such as a luggage may be used instead of an anatomical organ 206 to generate the scanned data 106. The scanned data 106 includes a plurality of electrical signals corresponding to the plurality of detector elements, representative of the intensity of an impinging x-ray beam and hence the attenuation of the beam as it passes through the organ 206. In one embodiment, the scanned data 106 includes sinogram data. In one embodiment, the sinogram data may correspond to dual energy CT sinogram data or to multiple sets of CT sinogram data acquired in sequence over multiple time instants.

During scanning, the gantry and the components mounted thereon rotate about a center of rotation of the subject 130. In one embodiment, the detector elements are layered structures configured to provide energy resolved electrical signals. In one embodiment, the energy resolved electrical signals are representative of a plurality of photon counts corresponding to a plurality of energy thresholds set by a photon-counting detector. The energy resolved electrical signals have superior capability of representing finer material densities of objects such as internal organs of the subject. The rotation of the gantry and the operation of the x-ray source are governed by a control mechanism of the CT imaging system 200. The control mechanism includes an x-ray controller 210 that provides power and timing signals to the x-ray source and a gantry motor controller 212 that controls the rotational speed and position of the gantry. In addition, computer operates a table controller 214 which controls a motorized table to position the subject in the gantry. In embodiments where the gantry 102 is a CT imaging system, a series of 2D projections are acquired as the scanned data 106. In other embodiments, the scanned data 106 includes 3D dataset corresponding to a volume under examination and 4D dataset corresponding to a temporal acquisition of the volume. The projections are representative of a set of projection views from which a reconstructed set of cross-sectional images, a three-dimensional (3D) image volume or a 4D image volume may be reconstructed.

Further, the CT imaging system is communicatively coupled to the diagnostic sub-system 104 that is configured to control the control mechanisms 210 212, 214 and generate the diagnostic output 108. The diagnostic sub-system 104 of FIG. 1 (and FIG. 2) includes a data acquisition unit 110, an image processor 112, a deep learning network 114, a processor 116 and a memory module 118 interconnected with each other by a communications bus 128. As stated previously, the diagnostic sub-system 104 is configured to receive the scanned data and generate the diagnostic output 108.

The data acquisition unit 110 is communicatively coupled to the detector 208 and configured to acquire the scanned data 106. In one embodiment, the scanned data 106 includes sinogram data. The data acquisition unit 110 is configured to perform bandwidth limiting, noise filtering and analog-to-digital conversion of the scanned data. The data acquisition unit 110 is configured to store the scanned data in the memory module 118. In some embodiments, the data acquisition unit 110 is also configured to retrieve stored scanned data corresponding to different time instants for processing. In one embodiment, the data acquisition unit 110 is further configured to receive photon count data obtained from a computed tomography detector. The image processor 112 is communicatively coupled to the data acquisition unit 110 and configured to generate a reconstructed image generally represented by reference numeral 124. In one embodiment, the image processor 112 is configured to receive sampled and digitized scanned data from the data acquisition unit 110 and perform high speed image reconstruction. The reconstructed image is stored in the memory module or displayed to a medical professional or further processed to characterize an anatomical feature corresponding to the subject.

In one embodiment, the image processor 112 is configured to identify a first region in a cross-sectional image corresponding to the image data. The first region is representative of a region of interest corresponding to an anatomical organ of the subject or a medical condition. The image processor 112 is further configured to identify image data present within the first region. The term 'regional data' is used herein to refer to the image data present within the first region. The image processor 112 is further configured to determine a second region in a projection of the scanned data. The second region in the scanned data corresponds to the first region of the image data. In one embodiment, the image processor 112 is further configured to identify a sinogram trace corresponding to the regional data. The sinogram trace is obtained by projecting the regional data. It may be noted herein that the image data includes the regional data and the sinogram data includes the sinogram trace. The second region in the sinogram data is representative of the first region in the image data. In another embodiment, the sinogram trace is extracted from a difference sinogram that is the difference between a first sinogram trace and a second sinogram trace. The first sinogram trace comprises scanned data from the second region and the second sinogram trace is derived from the first sinogram trace. In one embodiment, a first image is obtained by reconstructing the first sinogram trace. An image mask is applied to the first image to obtain a background image. The background image does not include image information corresponding to the region of interest. The image mask is applied by setting pixel values of the first image present in the region of interest to a constant value. Further, the second sinogram is obtained by projecting the background image. While in some embodiments the sinogram trace is obtained by projecting the regional data onto the detector for a plurality of projection angles, in other embodiments, the sinogram trace may also be obtained by projecting the region of interest in the first image corresponding to one of the plurality of projection angles. It may be noted that in one embodiment, the region of interest may be determined by an automatic segmentation technique. In another embodiment, the region of interest may be obtained by a manual or semi-manual image processing technique. In one embodiment, the image processor is configured to generate a third sinogram trace as a difference of the first sinogram trace and the second sinogram trace. The third sinogram trace is representative of a sinogram of the region of interest.

The deep learning network 114 is communicatively coupled to the image processor 112 and the data acquisition unit 110 and configured to determine a data feature corresponding to the region of interest. In one embodiment, the deep learning network is a convolutional neural network having machine learning ability. In one embodiment, the deep learning network 114 is configured to receive the scanned data 106 and the reconstructed image data 124 and generate the diagnostic output 108. In one embodiment, the diagnostic output 108 is a data feature. In one embodiment, the data feature is an anatomical feature representative of an anatomical condition. Non-limiting examples of the anatomical feature may include one or more of a bone region, a tumor, a stenosis condition, a plaque, a calcium deposit, a nodule, a lesion. In another embodiment, the data feature includes a physiological condition such as, but not limited to, a bleeding condition, a motion field and contrast agent dynamics. In another embodiment, the data feature includes a pathological condition using diagnosis and/or prognosis. In certain embodiments, in addition to one or more of the anatomical feature, physiological condition and pathological condition, the diagnostic output 108 may further include a description of the data feature. Non-limiting examples of the data feature may include a quantitative measure, a descriptive measure, and a classification category of the data feature.

In one embodiment, the deep learning network 114 includes a plurality of convolution stages and a connected neural network. Further, each of the plurality of convolution stages includes at least one of a feature generator, also referred to as a "convolution layer," an activation layer and a pooling layer. The feature generator is configured to transform input data to generate a plurality of features in the form of a feature map. In one embodiment, the input data is a plurality of 2D datasets. A plurality of 3D filters is used to transform the input data to generate the feature map having a plurality of 3D features. The activation layer is configured to transform the plurality of features with non-linear activation functions. In one embodiment, the activation function is a sigmoid function applied elementwise in the activation layer. In another embodiment, the activation function is a rectified linear unit (RELU) function applied elementwise in the activation layer. The pooling layer is configured to subsample the 2D data in spatial dimensions. The output of the pooling layer is a feature map of reduced dimensionality.

The deep learning network is trained to generate and/or characterize an anatomical feature corresponding to the region of interest. The training of the deep learning network is performed using a variety of known training techniques such as, but not limited to, a gradient descent method, a back-propagation method and least squares method. The training method employs regularization techniques to avoid overfitting. In some embodiments, regularization techniques, such as, but not limited to, L1 norm regularization and L2 norm regularization are used to avoid overfitting. In one exemplary embodiment, the deep learning network includes a dropout layer in the convolution stage for regularization. The dropout layer is configured to select a subset of available neuron elements for the training purposes and thereby, the dropout layer may decrease an amount of interactions between neuron elements.

In one embodiment, the deep learning network is configured to process sinogram data present within the second region and determine the data feature. In another embodiment, the deep learning network is configured to process image data present within the first region along with the sinogram data present within the second region to determine the data feature. As stated previously, the sinogram trace is a portion of the sinogram data corresponding to the first region. The regional data is a portion of the image data corresponding to an organ of interest or a medical condition, present within the first region. The deep learning network is further configured to generate at least one of a diagnostic condition and a treatment plan corresponding to a medical condition of the subject based on the data feature. In one embodiment, the deep learning network is configured to detect at least one of a tumor condition, a stenosis condition, a plaque, a bleeding condition, a nodule, a calcium deposit, a motion field and a lesion. In another embodiment, the deep learning network is further configured to determine at least one of a quantitative measure, a descriptive measure, and a classification of the diagnostic condition.

The processor 116 includes at least one of a general-purpose computer, a GPU, a digital signal processor, a controller. In other embodiments, the processor 116 includes a customized processor element such as, but not limited to, ASIC and FPGA. The processor 116 may be further configured to receive commands and scanning parameters from an operator via console that has a keyboard or a mouse or any other input device. The processor 116 may also be configured to provide one or more outputs such as, but not limited to, an audio, visual or tactile sensory signals. The processor 116 may be further configured to allow the operator to observe the reconstructed image 124 and the diagnostic output 108 from the diagnostic sub-system 104 via an associated display device. The operator supplied commands and parameters are used by the processor 116 to provide control signals and information to the DAS and the gantry 102. In some embodiments, the processor 116 may perform one or more functions of at least one of the data acquisition unit 110, the image processor 112 and the deep learning network 114. The processor 116 may include more than one processor co-operatively working with each other for performing intended functionalities. The processor 116 is further configured to store (retrieve) contents into (from) the memory module 118. In one embodiment, the processor 116 is configured to initiate and control the functionality of at least one of the data acquisition unit 110, the image processor 112 and the deep learning network 114.

In one embodiment, the memory module 118 is a random access memory (RAM), read only memory (ROM), flash memory or any other type of computer readable memory accessible by at least one of the data acquisition unit 110, the image processor 112 and the deep learning network 114. In one embodiment, the memory module 118 may be a non-transitory computer readable mediums encoded with a program having a plurality of instructions to instruct at least one of the data acquisition unit 110, the image processor 112 and the deep learning network 114 to perform a sequence of steps to characterize a feature of the subject. The program may further instruct the diagnostic sub-system 104 to generate a diagnostic image during scanning of the object.

Specifically, the plurality of instructions provided by the memory module 118 enables the data acquisition unit 110 to receive scanned data 106 corresponding to the subject as well as image data corresponding to the subject. The scanned data 106 comprises the sinogram data. The instructions further enable the image processor 112 to identify a first region in a cross-sectional image of the image data. In one embodiment, the instructions may further enable the image processor 112 to identify the image data present within the first region as the regional data. The regional data is a portion of the image data corresponding to an organ of interest or a medical condition in the subject. The instructions further enable the image processor 112 to determine a second region in a projection view of the sinogram data corresponding to the first region in the image data. The instructions enable the image processor 112 to determine a sinogram trace based on the second region and the sinogram data. The instructions also enable the deep learning network 114 to determine a data feature of the subject based on the sinogram trace and a deep learning network. The instructions also enable the deep learning network 114 to generate at least one of a diagnostic condition and a treatment plan corresponding to a medical condition of the subject based on the data feature.

Figure 3:
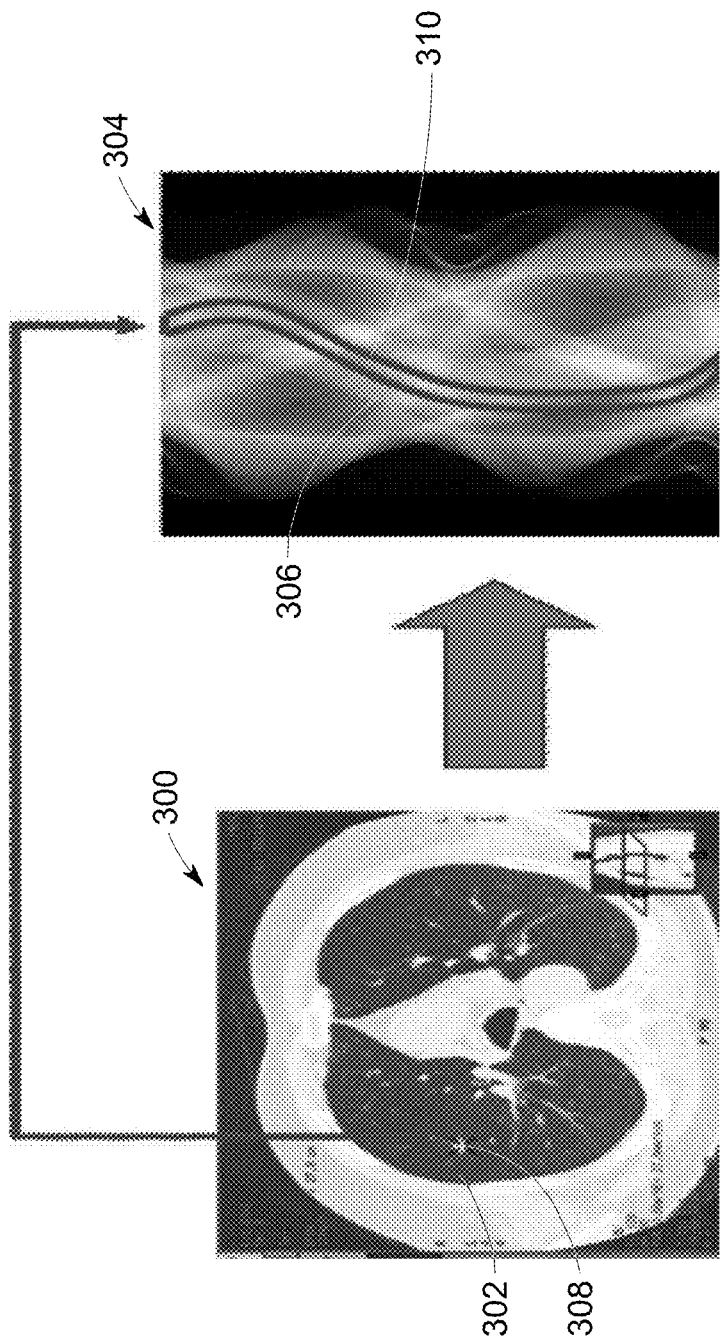
FIG. 3A is an image illustrating a region of interest in reconstructed image data used for characterizing a data feature in accordance with an exemplary embodiment.
FIG. 3B is an image illustrating the region of interest of FIG. 3A in scanned data used for characterizing a data feature in accordance with an exemplary embodiment.

FIG. 3A shows an image 300 illustrating a region of interest in reconstructed image data used for characterizing an anatomical feature in accordance with an exemplary embodiment of the present specification. The reconstructed image 300 is representative of an anatomy in the reconstructed image data. A first region 302 representative of a region of interest, is identified in the reconstructed image 300. The image data present within the first region 302 in the image 300 is illustrated as regional data 308. It may be noted herein that the regional data 308 present within the first region 302 is provided to the deep learning network 114 for characterizing the anatomical feature.

FIG. 3B is a sinogram 304 illustrating the region of interest in the scanned data used for characterizing an anatomical feature in accordance with an exemplary embodiment of the present specification. The sinogram 304 is representative of a projection of the anatomy in the scanned data. In the illustrated embodiment, the sinogram 304 corresponds to the image 300 of FIG. 3A. A second region 306 representative of the region of interest corresponding to the first region 302, is identified in the sinogram 304. The scanned data present within the second region 306 in the sinogram 304 is illustrated as sinogram trace 310. The sinogram trace 310 present within the second region 306 is determined by projecting the regional data 308 present within the first region 302. In some embodiments, the sinogram trace 310 is provided to the deep learning network 114 for characterizing anatomical feature of the region of interest. In other embodiments, both the sinogram trace 310 and the regional data 308 are provided to the deep learning network 114 for characterizing anatomical feature of the region of interest.

Figure 4:
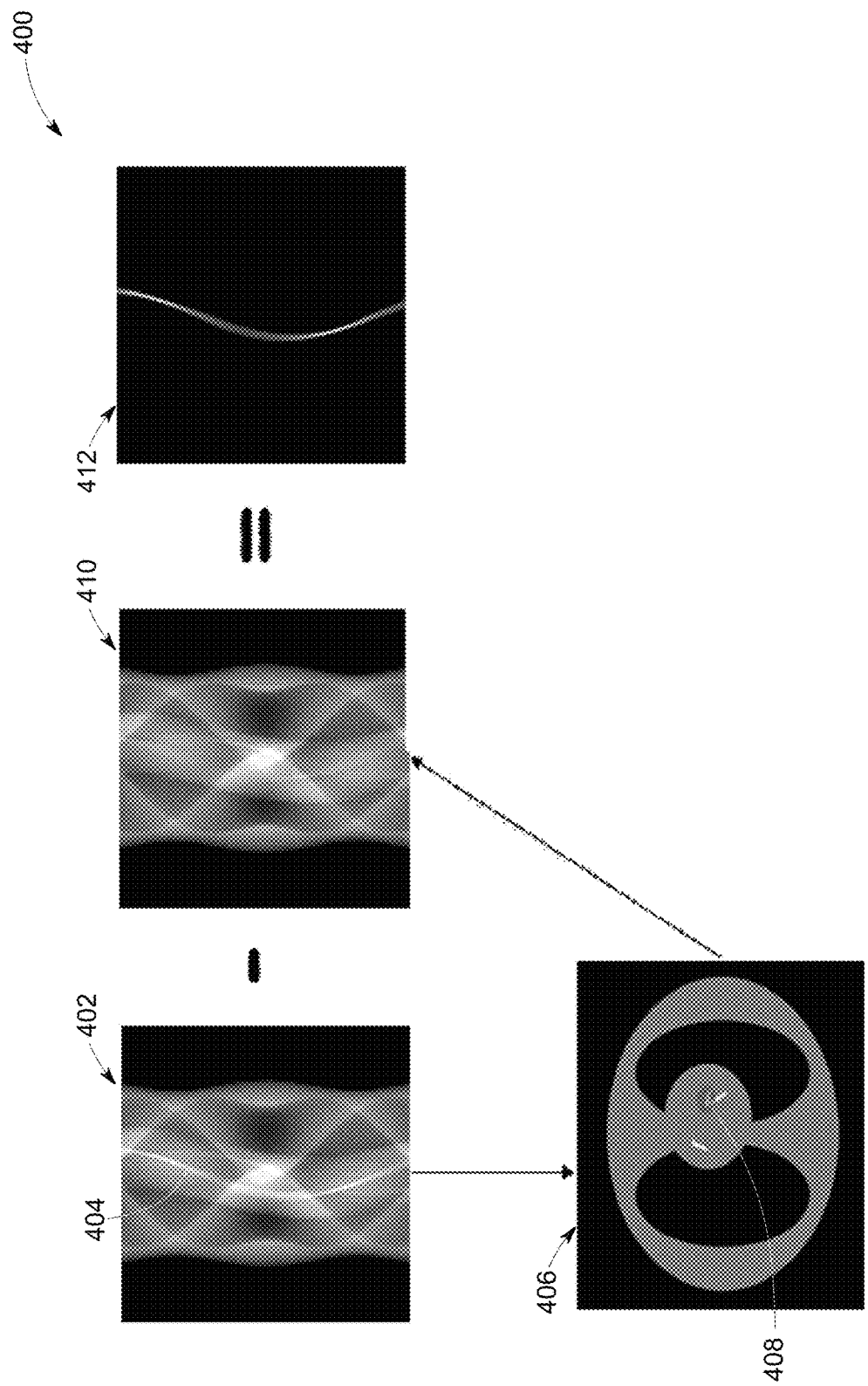
FIG. 4 illustrates processing steps involved in determining scanned data corresponding to the region of interest in accordance with an exemplary embodiment.

FIG. 4 is a workflow diagram 400 illustrating processing steps involved in determining a sinogram trace in accordance with an exemplary embodiment. The workflow diagram 400 includes input sinogram 402 having a known region of interest 404. A reconstructed image 406 corresponding to the sinogram 402 is obtained by processing the sinogram 402 using a filtered back projection technique. A mask image 408 designed to cover the known region of interest is used to generate a background image from the reconstructed image. The background image excludes reconstructed image data in the region of interest. In some embodiments, the reconstructed image data in the region of interest may be replaced by other values, such as by a constant value. A corresponding background sinogram 410 is obtained by processing the background image using a forward projection technique. In one example, a Radon transformation or an X-ray cone-beam transformation is used for processing the background image. A difference between the input sinogram 402 and the background sinogram 410 is determined to generate a sinogram corresponding only to the region of interest 412. In one embodiment, the sinogram for the region of interest is provided to the deep learning network 114 for characterizing anatomical features of the region of interest.

Figure 5:
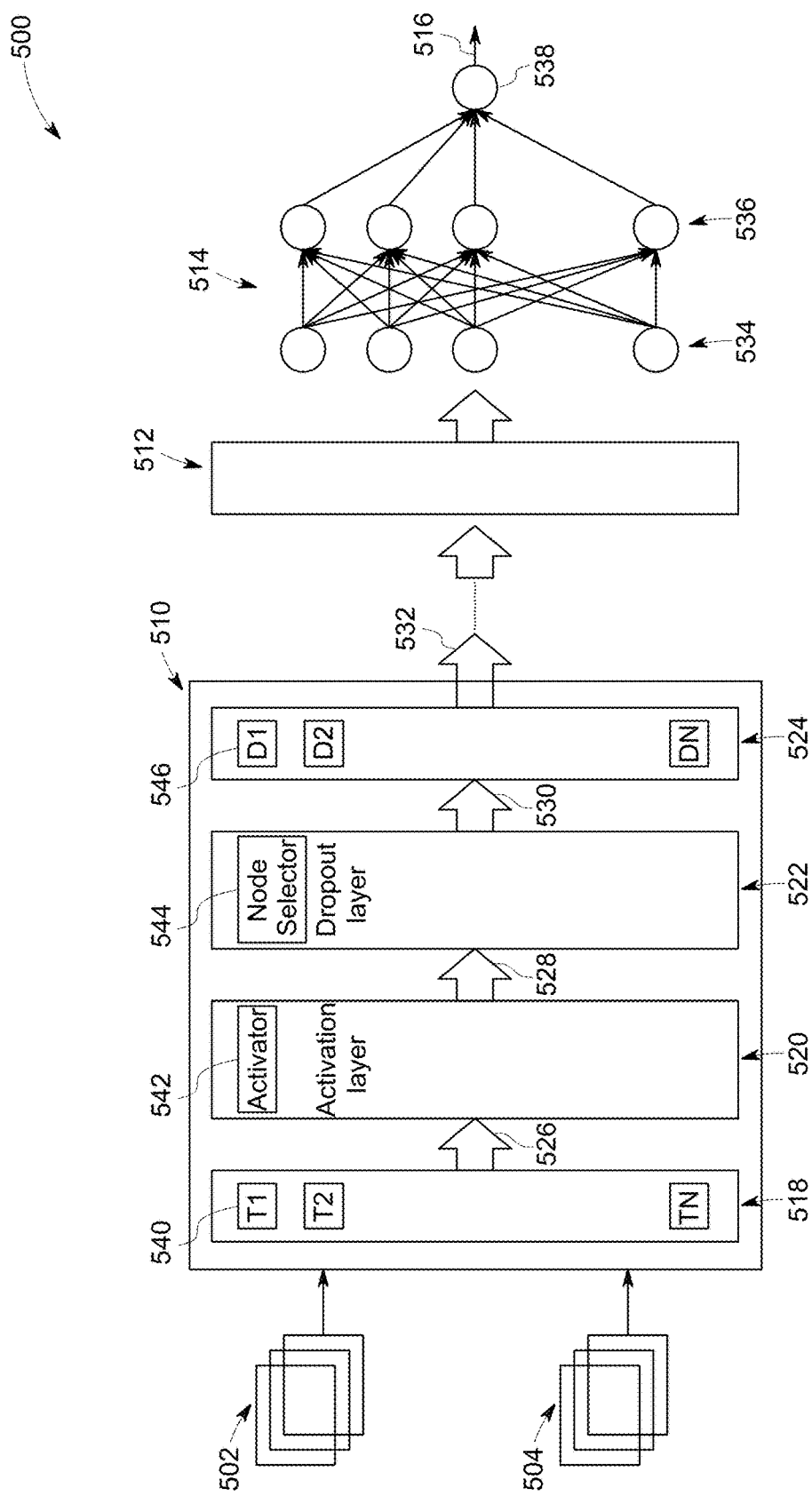
FIG. 5 is a schematic representation of a deep learning network utilizing scanned data in accordance with an exemplary embodiment.

FIG. 5 is a schematic of a deep learning network 500 utilizing scanned data in accordance with an exemplary embodiment. The deep learning network 500 in the illustrated embodiment is a convolution neural network. The deep learning network 500 includes a plurality of convolution stages 510, 512 and a connected neural network 514. A first convolution stage 510 includes a first feature generator 518 in cascade with a first activation layer 520. Further, the first convolution stage 510 includes a first dropout layer 522 and a first sub sampling stage 524. The first convolution stage 510 is configured to receive sinogram data 504 and generate a first plurality of feature maps 532. In some embodiments, the first convolution stage 510 is configured to receive image data 502 in addition to the sinogram data 504. Specifically, the first feature generator 518 includes a first plurality of feature transformers 540 and is configured to generate a first plurality of feature maps 526. The first activation layer 520 processes the first plurality of feature maps 526 in a non-linear fashion. The non-linear processing is performed based on functions such as, but not limited to, a sigmoid function and a piecewise linear cutoff function. In one embodiment of the first activation layer 520, each element of the plurality of feature maps 526 is processed by an activator 542 based on a sigmoid function. In another embodiment of the first activation layer 520, each element of the plurality of feature maps 526 is processed by the activator 542 based on a RELU function. The first activation layer 520 is configured to generate a plurality of second feature maps 528 based on the first plurality of feature maps 526.

Further, the first dropout layer 522 of the first convolution stage 510 is configured to operate on the second plurality of feature maps 528 to generate a third plurality of feature maps 530. In one embodiment, the first dropout layer 522 includes a node selector 544 for identifying a subset of available nodes and configured to selectively train the identified nodes. The first sub sampling stage 524 includes a plurality of spatial samplers 546 configured to generate a subsampled version of the third plurality of feature maps 530 as a fourth plurality of feature maps 532. The deep learning network 500 further includes a second convolution stage 512 having a second feature generator, a second activation layer, a second dropout layer and a second sub sampling stage (internal details are not shown). Although only two convolution stages 510, 512 are shown in the illustrated embodiment, there may be many more such convolution stages in the deep learning network 500.

The neural network 514 includes an input layer 534 having a plurality of input nodes and at least one output node 538. A hidden layer 536 having a plurality of hidden nodes may be present in cascade with the input layer 534. In one embodiment, the input layer 534 is representative of data vector formed based on the elements of the second subsampling stage using a serialization operation. Similarly, the hidden layer 536 is representative of a data vector representative of an intermediate feature map. The output node 538 is representative of an output determined based on a linear combination of the elements of the intermediate feature vector. The transformed value at the output node 516 is representative of characterization of an anatomical feature in a region of the subject. The plurality of convolution stages extracts features from the sinogram data 504 in stages that are helpful in performing the intended task of the convolution neural network.

Figure 6:
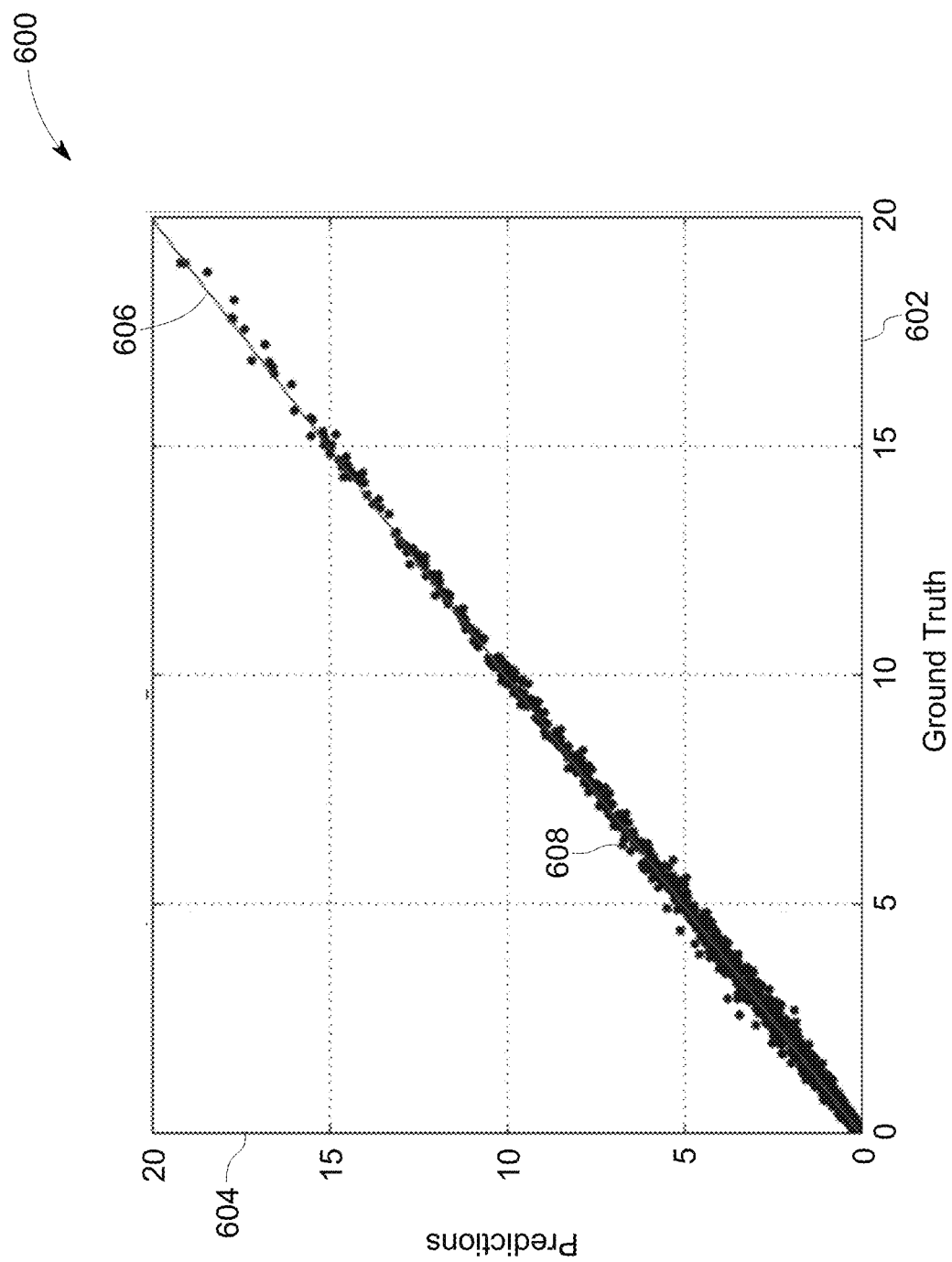
FIG. 6 is a graphical representation of performance of the system of FIG. 1 in accordance with an exemplary embodiment.

FIG. 6 is a graph 600 representative of performance of the system of FIG. 1 in accordance with an exemplary embodiment. The graph 600 includes an x-axis 602 representative of true values of data feature and a y-axis 604 representative of estimated values of data feature using a deep learning network. The data feature considered in this example is a cross sectional area of an ellipse with major and minor axis diameters having a uniform distribution in a range of 0 to 5 millimeters. The center of ellipse is randomly located in an x-y plane with coordinates chosen from a uniform distribution in a range from −2 to +2 millimeters.

In the simulations, about 30000 phantoms having different density values are created with different ellipsoidal positions and dimensions. The phantoms are projected using 2D parallel beam geometry and the projections are captured by a detector row having ten columns. In one rotation, about 41 views of projections are generated. The sinogram data includes 2D projections having 10 pixels along the width direction and 41 pixels along the length direction. A deep learning network in the form of a fully connected neural network layer having three hidden layers is used for estimating the data feature. The deep learning network includes an input layer having 41 input nodes and one output node generating a real value output representative of area of the ellipsoid. A plurality of filters is used to generate a plurality of neurons in the hidden layers. Each of the plurality of layers also have the size of the projections of the sinogram data.

The deep learning network is trained with a sample size of 30000 and the trained deep learning network is validated using 1000 test sinogram projections. The graph 600 includes a cluster of points 608 representative of estimated area values of ellipsoids represented in the test sinogram projections. The cluster of points 608 is closely aligned to a line 606 having a unity slope indicating accuracy in the estimation.

Figure 7:
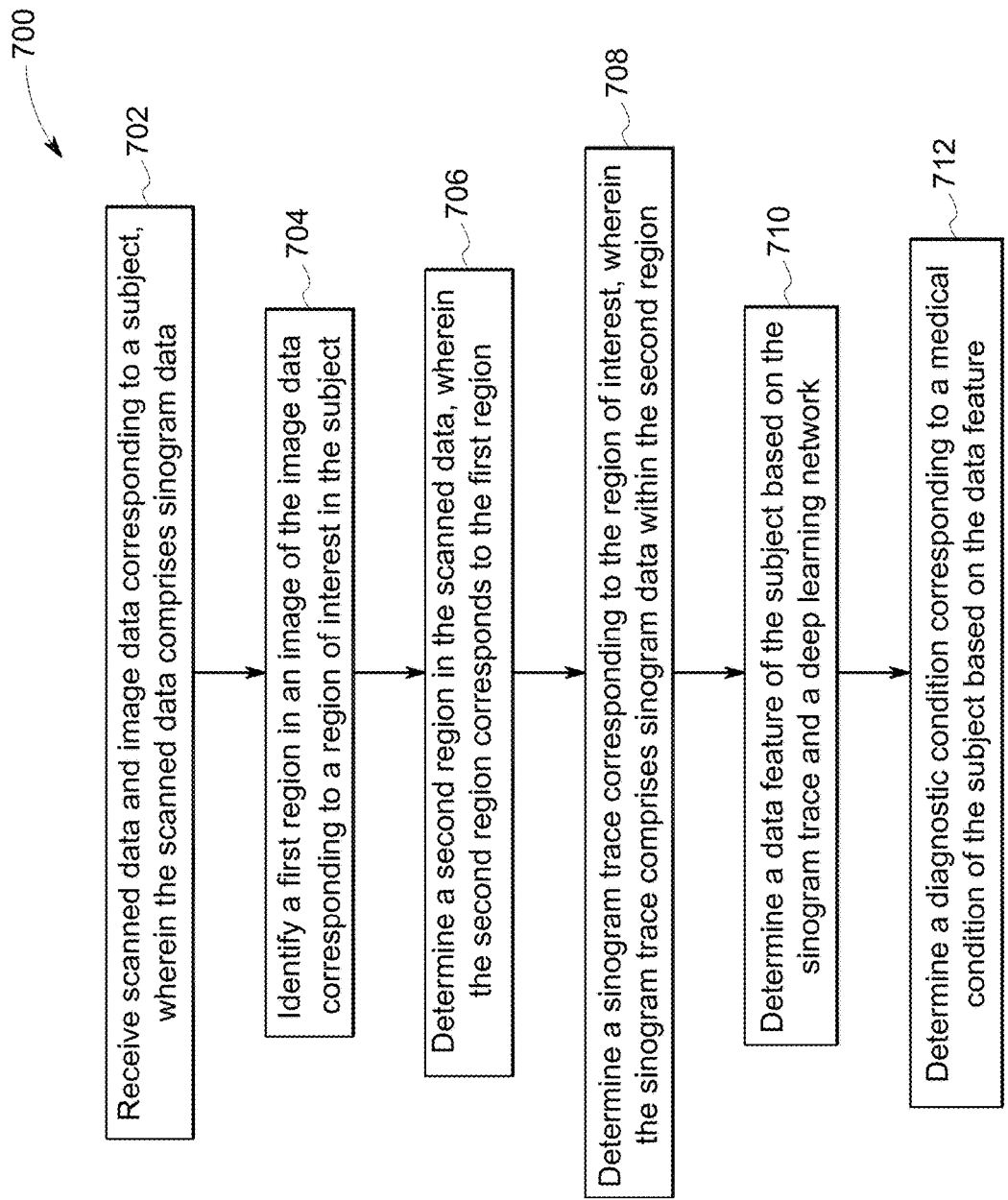
FIG. 7 is a flow chart of a method of characterization of data features in accordance with an exemplary embodiment.

FIG. 7 is a flow chart 700 of a method for characterization of anatomical features in accordance with an exemplary embodiment. The method includes receiving scanned data and image data corresponding to a subject at block 702. The scanned data includes sinogram data. In one embodiment, the sinogram data includes photon count data obtained from a photon-counting CT detector.

The method further includes identifying a first region in an image of the image data corresponding to a region of interest in the subject in block 704. In one embodiment, the first region is identified or known a priori and corresponds to the region of interest in the image data. In one embodiment, the first region is determined by an automated segmentation technique. In another embodiment, the first region is determined manually by a user/human observer. The image data present within the first region is referred herein as the 'regional data'.

In block 706, the method further includes determining a second region in the scanned data based on the first region. Specifically, the second region is a region in a projection view of the scanned data corresponding to the first region. In one embodiment, the second region is determined based on one-to-one correspondence between the image data and the sinogram data. The second region in the scanned data corresponds to the first region in the image data. The method further includes determining a sinogram trace corresponding to the region of interest in step 708. The term 'sinogram trace' used herein refers to sinogram data present within the second region. Specifically, the sinogram trace is the scanned data corresponding to a second region in a projection view corresponding to the subject. In one embodiment, determining the sinogram trace includes projecting the regional data for a plurality of projection angles. The second region in the projection views corresponds to the first region in the image.

In another embodiment, the step of determining the sinogram trace includes determining a first image by reconstructing a first sinogram. Further, an image mask covering the region of interest in the image data is used to generate a background image from the first image. The background image includes background information of the first image and does not include the region of interest, but may replace the region of interest by other values, such as by a constant value. A second sinogram is determined by reprojecting the background image. In one embodiment where motion is present in the subject, a plurality of reconstructions corresponding to a single rotation, is considered for generating the second sinogram. In an example of cardiac imaging, the reprojection may consider the cardiac phase information while generating the second sinogram. A third sinogram is determined as a difference between the first sinogram and the second sinogram. The third sinogram is representative of the region of the interest and does not contain the background image information. In this embodiment, the sinogram trace is equivalent to the third sinogram. In another embodiment, determining the second region includes projecting the region of interest in the image data. The sinogram trace is generated by extracting the sinogram data inside the second region.

In block 710, the method further includes determining a data feature of the subject based on the sinogram trace and a deep learning network. In one embodiment, a deep learning network such as, but not limited to, a convolution neural network, is used to determine the anatomical feature as the data feature. The deep learning network is trained to determine the data features using a plurality of simulated sinogram datasets having known data features. In one embodiment, the anatomical feature includes identification of an anatomical condition such as, but not limited to, a tumor, a stenosis condition, a plaque, a bleeding condition, a nodule, a lesion, a motion field and a calcium deposit. It may be noted that the data feature may represent a physiological or pathological characterization of an anatomical organ. In another embodiment, the anatomical feature further includes a description of the anatomical condition such as, but not limited to, a quantitative measure, a descriptive measure, and a classification of the diagnostic condition. The method further includes generating a diagnostic condition corresponding to a medical condition of the subject based on the anatomical feature as illustrated in block 712. Further, at step 712, a treatment plan may also be generated based on the diagnostic condition. In one embodiment, the method further includes processing the first region using the deep learning network. In one embodiment, determining the data feature includes training the deep learning network using a plurality of simulated sinogram datasets having known data features.

It is to be understood that not necessarily all such objects or advantages described above may be achieved in accordance with a particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:
1. A method, comprising:
receiving scanned data and image data corresponding to a subject, wherein the scanned data comprises sinogram data;
identifying a first region in an image of the image data corresponding to a region of interest;

determining a second region in the scanned data, wherein the second region corresponds to the first region;

identifying a sinogram trace corresponding to the region of interest, wherein the sinogram trace comprises sinogram data present within the second region;

characterizing an anatomical feature corresponding to the region of interest of the subject based on the sinogram trace and a trained deep learning network; and determining a diagnostic condition corresponding to a medical condition of the subject based on the anatomical feature, wherein identifying the sinogram comprises projecting the image data present within the first region using a Radon transformation.

2. The method of claim 1, further comprising processing the image data present within the first region using the trained deep learning network.

3. The method of claim 1, wherein the image data is generated by reconstructing the scanned data based on input from an operator on a display device.

4. The method of claim 1, wherein identifying the sinogram trace comprises:

applying an image mask to the image data present within the first region to generate a background image, wherein the background image does not comprise the region of interest;

determining a second sinogram trace by projecting the background image; and generating a third sinogram trace as a difference of a first sinogram trace and the second sinogram trace, wherein the third sinogram trace is representative of a sinogram of the region of interest.

5. The method of claim 1, wherein the first region is determined by an automated segmentation technique.

6. The method of claim 1, wherein the sinogram data further comprises photon count data obtained from a photon-counting CT detector.

7. The method of claim 1, wherein the anatomical feature comprises at least one of a tumor, a stenosis condition, a plaque, a nodule, a lesion, a bleeding condition and a motion field.

8. The method of claim 7, wherein the anatomical feature further comprises at least one of a quantitative measure, a descriptive measure, and a classification of the diagnostic condition.

9. The method of claim 1, wherein determining the anatomical feature comprises training the deep learning network using a plurality of simulated sinogram traces having known anatomical features.

10. A system, comprising:

a data acquisition unit configured to acquire scanned data and image data corresponding to a subject, from a computed tomography detector, wherein the scanned data comprises sinogram data;

an image processor communicatively coupled to the data acquisition unit and configured to:

identify a first region in an image of the image data corresponding to a region of interest in the subject;

determine a second region in the scanned data, wherein the second region corresponds to the first region;

determine a sinogram trace corresponding to the region of interest, wherein the sinogram trace comprises sinogram data present within the second region, wherein identifying the sinogram comprises projecting the image data present within the first region using a Radon transformation;

a trained deep learning network communicatively coupled to the image processor and configured to:

characterize an anatomical feature corresponding to the region of interest of the subject based on the sinogram trace; and determine a diagnostic condition corresponding to a medical condition of the subject based on the anatomical feature.

11. The system of claim 10, wherein the trained deep learning network is further configured to process the image data present within the first region to characterize the anatomical feature of the subject.

12. The system of claim 10, wherein the image processor is further configured to:

apply an image mask to the image data present within the first region to generate a background image, wherein the background image does not comprise the region of interest;

determine a second sinogram trace by projecting the background image; and generate a third sinogram trace as a difference of a first sinogram trace and the second sinogram trace, wherein the third sinogram trace is representative of a sinogram of the region of interest.

13. The system of claim 10, wherein the image processor is further configured to generate the image data by reconstructing the scanned data based on input from an operator on a display device.

14. The system of claim 13, wherein the image processor is further configured to determine the image data present within the first region using an automated segmentation technique.

15. The system of claim 10, wherein the trained deep learning network is configured to detect at least one of a tumor condition, a stenosis condition, a plaque, a nodule, a lesion, a bleeding condition, and a motion field.

16. The system of claim 15, wherein the trained deep learning network is further configured to determine at least one of a quantitative measure, a descriptive measure, and a classification of the diagnostic condition.

17. A computed tomography imaging system, comprising:

an x-ray source configured to emit x-ray beam towards an organ during examination of a subject;

a computed tomography detector configured to receive the emitted x-ray beam attenuated by the region to generate scanned data;

a data acquisition unit configured to acquire the scanned data from the computed tomography detector, wherein the scanned data comprises sinogram data;

an image processor communicatively coupled to the data acquisition unit and configured to:

generate image data by reconstructing the scanned data based on input from an operator on a display device;

identify a first region in an image of the image data corresponding to a region of interest in the subject;

determine a second region in the scanned data, wherein the second region corresponds to the first region;

determine a sinogram trace corresponding to the region of interest, wherein the sinogram trace comprises sinogram data present within the second region, wherein identifying the sinogram comprises projecting the image data present within the first region using a Radon transformation;

a trained deep learning network communicatively coupled to the image processor and configured to:

characterize an anatomical feature of the region based on the sinogram trace; and determine a diagnostic condition corresponding to a medical condition of the subject based on the anatomical feature.

18. A non-transitory computer readable medium having instructions to enable at least one processor module to:
receive scanned data and image data corresponding to a subject, wherein the scanned data comprises sinogram data and the image data is generated by reconstructing the scanned data based on input from an operator on a display device;
identify a first region in an image of the image data corresponding to a region of interest in the subject;
determine a second region in the scanned data, wherein the second region corresponds to the first region;
determine a sinogram trace corresponding to the region of interest, wherein the sinogram trace comprises sinogram data present within the second region;
characterize an anatomical feature corresponding to the region of interest of the subject based on the sinogram trace and a trained deep learning network; and
determine a diagnostic condition corresponding to a medical condition of the subject based on the anatomical feature, wherein identifying the sinogram comprises projecting the image data present within the first region using a Radon transformation.

* * * * *